(12) United States Patent
Datta et al.

(10) Patent No.: US 8,212,093 B2
(45) Date of Patent: Jul. 3, 2012

(54) OLEFIN PRODUCTION FROM SYNGAS BY AN INTEGRATED BIOLOGICAL CONVERSION PROCESS

(75) Inventors: Rathin Datta, Warrenville, IL (US); Richard E. Tobey, St. Charles, IL (US); Rahul Basu, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 601 days.

(21) Appl. No.: 12/468,695

(22) Filed: May 19, 2009

(65) Prior Publication Data
US 2010/0294642 A1 Nov. 25, 2010

(51) Int. Cl.
*C07C 4/00* (2006.01)
*C12M 1/12* (2006.01)
*C12P 7/08* (2006.01)

(52) U.S. Cl. ..... 585/240; 435/163; 435/170; 435/297.4; 210/321.79; 585/242

(58) Field of Classification Search ............ 585/240, 585/242; 435/397.4, 170, 286.6, 297.3, 163; 210/321.79
See application file for complete search history.

(56) References Cited

U.S. PATENT DOCUMENTS

| | | | |
|---|---|---|---|
| 4,336,335 A | 6/1982 | Muller et al. | |
| 4,455,394 A | 6/1984 | Pinto | |
| 5,173,429 A | 12/1992 | Gaddy et al. | |
| 6,133,328 A * | 10/2000 | Lightner | 518/700 |
| 6,136,577 A | 10/2000 | Gaddy | |
| 6,340,581 B1 | 1/2002 | Gaddy | |
| 6,919,488 B2 | 7/2005 | Melnichuk et al. | |
| 7,118,672 B2 | 10/2006 | Husain et al. | |
| 7,199,276 B2 | 4/2007 | Sher et al. | |
| 7,285,402 B2 | 10/2007 | Gaddy et al. | |
| 7,288,689 B2 | 10/2007 | Janssen et al. | |
| 7,309,592 B2 | 12/2007 | Offerman et al. | |
| 8,017,384 B2 * | 9/2011 | Tsai et al. | 435/297.4 |
| 8,058,058 B2 * | 11/2011 | Hickey et al. | 435/297.4 |

(Continued)

FOREIGN PATENT DOCUMENTS

WO WO2008154301 12/2008

OTHER PUBLICATIONS

Mississippi Ethanol LLC; Final Report from Mississippi Ethanol LLC to the National Renewable Energy Laboratory; Subcontractor Report; Mar. 2002; NREL/SR-510-31720; Golden, CO.

(Continued)

*Primary Examiner* — Nina Bhat
(74) *Attorney, Agent, or Firm* — Cardinal Law Group

(57) ABSTRACT

The production of feed for an olefin hydration zone is improved by integrating treatment of an alcohol containing stream from a fermentation zone into an alcohol separation section. The process passes a stream comprising alcohol, water and an organic acid to a separation column. The separation column concetrates the alcohol and organic acids into an upper column fraction. An additive for neutralization the organic acid into contact with said upper column fraction and reacts with the organic acid to produce a neutralization product that passes to a lower portion of the separation column. The column provides an overhead stream for an olefin dehydration zone having an increased concentration of alcohol and a reduced concentration of organic acid. A column bottoms stream containing the neutralization product returns as an input stream to supply the neutralization product to a fermentation zone that produces the alcohol containing stream.

21 Claims, 2 Drawing Sheets

U.S. PATENT DOCUMENTS

| | | | |
|---|---|---|---|
| 8,062,873 B2* | 11/2011 | Tsai et al. ............... 435/170 |
| 2004/0229343 A1* | 11/2004 | Husain et al. ............... 435/262 |
| 2007/0161095 A1* | 7/2007 | Gurin ............... 435/134 |
| 2007/0275447 A1* | 11/2007 | Lewis et al. ............... 435/161 |
| 2008/0033218 A1 | 2/2008 | Lattner et al. |
| 2008/0057554 A1 | 3/2008 | Huhnke et al. |
| 2008/0305539 A1 | 12/2008 | Hickey et al. |
| 2009/0029434 A1* | 1/2009 | Tsai et al. ............... 435/170 |
| 2009/0035848 A1 | 2/2009 | Hickey et al. |
| 2009/0104676 A1 | 4/2009 | Tsai et al. |
| 2009/0215139 A1 | 8/2009 | Datta et al. |
| 2009/0215142 A1 | 8/2009 | Tsai et al. |
| 2009/0215153 A1 | 8/2009 | Tsai et al. |
| 2009/0215163 A1 | 8/2009 | Tsai et al. |
| 2009/0286296 A1 | 11/2009 | Hickey et al. |

OTHER PUBLICATIONS

Rohit P. Datar, et al; Oklahoma State University; Fermentation of biomass-generated producer gas to ethanol; Published online Apr. 15, 2004; Wiley InterScience (www.interscience.wiley.com); DOI: 10.1002/bit.20071; Source: Biotechnology and Bioengineering Jun. 5, 2004;86(5):587-94.

U.S. Appl. No. 12/258,193, filed Oct. 24, 2008, Datta et al.

Clausen, E.G., et al., "Ethanol From Biomass by Gasification/Fermentation", Presented at Plastics, Tires, Auto Wastes/Biomass MSW Symposium, Fall 1993, Chicago, 38 (3).

Klasson, K.T., et al., "Biological Production of Liquid and Gaseous Fuels from Synthesis Gas," Appl. Biochem. Biotechnol., vol. 24-25, No. 1, Mar. 1990, 857-873.

Vega, J. L., et al., "The Biological Production of Ethanol from Synthesis Gas," Appl. Biochem. Biotechnol. vol. 20-21, No. 1, Jan. 1989, 781-797.

Phillips, John R., et al., "Synthesis Gas as Substrate for the Biological Production of Fuels and Chemicals," Appl. Biochem. Biotechnol. vol. 45-46, No. 1, Mar. 1994, 145-157.

Barik, S., et al., "Biological Production of Alcohols from Coal Through Indirect Liquefaction," Appl. Biochem. Biotechnol. vol. 18, No. 1, Aug. 1988, 363-387.

Henstra, A. et al., "Microbiology of synthesis gas fermentation for biofuel production," Current Opinion in Biotechnol., vol. 18, Mar. 2007, 200-206.

Abrini, J. et al., "*Clostridium autoethanogenum*, sp. nov., an anaerobic bacterium that produces ethanol from carbon monoxide," Arch. Microbiol. vol. 161, 1994, 345-351.

Das, A. and Ljungdahl, L.G., "Electron Transport System in Acetogens," Biochemistry and Physiology of Anaerobic Bacteria, 2003, 191-204, Springer-Verlag New York, Inc., New York, US.

Drake, H. and Kusel, K., "How the Diverse Physiologic Potentials of Acetogens Determine Their In Situ Realities," Biochemistry and Physiology of Anaerobic Bacteria, 2003, 171-190, Springer-Verlag New York, Inc., New York, US.

Grethlein, A. et al., "Evidence for Production of n-Butanol from Carbon Monoxide by *Butyribacterium methlyotrophicum*," J. Ferment. Bioeng., vol. 72, No. 1, 1991, 58-60.

Worden, R.M., et al., "Production of butanol and ethanol from synthesis gas via fermentation," Fuel. vol. 70, May 1991, 615-619.

* cited by examiner

OLEFIN PRODUCTION FROM SYNGAS BY AN INTEGRATED BIOLOGICAL CONVERSION PROCESS

FIELD OF THE INVENTION

This invention relates to the conversion of biomass into liquid products via fermentation and conversion of the liquid products into olefins.

DETAILED DESCRIPTION

Background

Olefins, particularly ethylene, are the backbone of the current petrochemical industry. Their present derivation relies primarily on catalytic cracking of petroleum or natural gas. These facilities require a lot of energy, very large and capital intensive operations and usage of the entire major byproducts made by these crackers.

Originally, dehydration of ethanol to ethylene was the commercial path before the advent of the petroleum age. Currently there is a very strong and renewed interest in producing chemicals from sustainable feedstocks and technologies. Fermentation of carbohydrate feedstocks such as sugar and starch to ethanol is well known, commercially practiced and can be readily utilized for ethylene. However, these feedstocks are derived from agricultural land and have competing use as food and animal feed.

Lignocellulosic feedstocks such as forest residues, trees from plantations, straws, grasses and other agricultural residues can also supply biomass for conversion into chemical products. Conversion of other renewable lignocellulosic feedstocks such as woody biomass via traditional pretreatment and fermentation technologies are inherently inefficient and do not give high yield and specificity to ethanol. The difficulty in using lignocellulosic materials stems from the very heterogeneous nature of these materials that enables them to provide the mechanical support structure of the plants and trees and makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers).

Technology has been developed to overcome this difficulty and convert lignocellulosic biomass to syngas (also known as synthesis gas, primarily a mix of CO, $H_2$, and $CO_2$ with other components such as $CH_4$, $N_2$, $NH_3$, $H_2S$, and other trace gases) and then ferment this gas with anaerobic microorganisms to produce bio-chemical liquids. This path can inherently provide more efficiency than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Thus syngas can be a very efficient technology, and 75 to 80% of the feedstocks' chemical energy content can be available in the syngas components with the rest available as high quality heat that can be used for process energy. Moreover, syngas can be made from many other carbonaceous feedstocks such as natural gas, reformed gas, peat, petroleum coke, coal, solid waste, and land fill gas, making this a more universal technology path.

The availability of syngas produced alcohols such as ethanol will increase the usefulness of alcohol dehydration for the production of olefins. One disadvantage of using fermentation process for the production of the olefins is the presence of organic acids in the fermentation broth. Organic acids pose problems for many of the catalyst systems for the dehydration of alcohols. For example acetate by-products present with the ethanol in fermentation broths will result in free acetic acid concentrations that can cause catalyst fouling in the dehydration zone. Finding ways to effectively and efficiently treat the alcohol containing streams from fermentation zones will simplify processes and improve the economics of producing olefins using alcohol from fermentation zones.

As a result there is a need to develop processes that improve the efficiency of converting alcohol derived from biomass into olefins. In particular there is a need to develop processes that convert ethanol or other alcohols with minor amounts of by-product organic acids and integrate efficient separation steps to deliver an alcohol stream of sufficient quality and purity for producing olefins from the alcohol.

SUMMARY OF THE INVENTION

It has now been discovered that processes for biologically converting biomass to ethanol or other alcohols can be advantageously integrated into a separation process that removes by-product organic acid and delivers an alcohol stream particularly suited for vapor phase dehydration of alcohol into a corresponding olefin. Accordingly this invention is an integrated process for the production of olefins, particularly ethylene, from carbonaceous feedstocks (that include renewable biomass) via syngas fermentation to alcohol and an integration of a separation process that delivers an alcohol stream of sufficient purity and water content for vapor phase catalytic dehydration.

In one embodiment the invention is a process for preparing an alcohol containing stream from an alcohol producing fermentation zone as a feed to an olefin reaction zone by removing organic acids. The process passes a stream comprising alcohol, water and an organic acid from a fermentation zone to a separation zone. The separation zone concentrates the alcohol and organic acid into an upper column fraction. An additive for neutralization of the organic acid is injected into contact with the upper column fraction. The additive reacts with the organic acid to produce a neutralization product that passes to a lower portion of a separation column in the separation zone. A column overhead is recovered from the separation zone and has an increased concentration of alcohol and a reduced concentration of the organic acid. At least a portion of the overhead stream is intended to pass to an olefin production zone to produce olefins from the alcohol. At least a portion of a column bottoms stream, recovered from the separation zone and containing the neutralization product, passes to an alcohol fermentation zone to provide neutralization product to the fermentation zone receiving the bottoms stream. The olefin production zone is preferably a dehydration zone for converting the alcohol to a corresponding olefin and more preferably the fermentation zone produces ethanol and the dehydration zone produces ethylene.

More specific embodiments will relate to specific stream compositions, additives and neutralization effects. For example addition of the neutralization additive will typically produce a bottoms stream with a pH in the range of from 5.5 to 8.0 and more typically in a range of from 6.0 to 7.0 and preferably will produce a bottoms stream with a pH of about 6.0. The neutralization additive can comprise sodium hydroxide so that reaction with the organic acid provides a sodium salt to the fermentation zone via the bottom stream. Other suitable alkali additives include potassium hydroxide and ammonium hydroxide. A more specific embodiment of the process employs a fermentation zone that converts syngas components into ethanol and the ethanol containing stream includes acetic acid so that reaction with the acetic acid in the separation zone produces a neutralization product comprising sodium acetate. The bottoms stream from the separation zone mixes with an aqueous fermentation broth to supply sodium acetate to the fermentation zone. In such cases the fermentation zone usually produces an effluent comprising water, 2 to 5 wt % ethanol, at least 0.3 wt % acetate and free acetic acid of at least 0.1 wt %. Ethanol will range from a concentration of 50 to 80 wt %, and more typically 70 to 80 wt %, in the column overhead which is relatively free of organic acid. As used herein the term relatively free of organic acid means an organic acid content of less then 0.01 wt %.

Another embodiment of this invention is a process for reducing organic acid in an ethanol containing stream from a syngas fermentation zone. The process passes a syngas stream containing at least one of CO or a mixture of $CO_2$ and $H_2$ to a fermentation zone and converts at least a portion of the syngas to ethanol. A fermentation stream comprising water, 2 to 5 wt % ethanol, at least 0.3 wt % acetate and free acetic acid of at least 0.1 wt % is withdrawn from the fermentation zone and passed to a separation column for concentrating the ethanol and organic acids into an upper column fraction. The process injects an additive for neutralization of the acetic acid into contact with the upper column fraction. The additive reacts with the acetic acid to produce a neutralization product that passes to a lower portion of the separation column. A column overhead relatively free of organic acid and having at least 50 wt % of ethanol is relatively free of organic acid is recovered from the separation column. A column bottoms stream containing said neutralization product is recovered from the separation zone and at least a portion of the column bottoms stream returns to an aqueous fermentation broth in the fermentation zone.

Another embodiment of the invention is a process for producing ethylene by reducing organic acid in an ethanol containing stream from a syngas fermentation zone and dehydrating the ethanol in an ethanol dehydration zone. The process passes a syngas stream containing at least one of CO or a mixture of $CO_2$ and $H_2$ to a fermentation zone and converting at least a portion of the syngas to ethanol. A fermentation stream withdrawn from the fermentation zone and comprising water, 2 to 5 wt % ethanol, at least 0.3 wt % acetate and free acetic acid of at least 0.1 wt % passes at least in part to a distillation column that concentrates the ethanol and organic acids into an upper column fraction. An additive injected into the upper column fraction for neutralization of the acetic acid reacts with the acetic acid to produce a neutralization product that passes to a lower portion of the distillation column. A column overhead relatively free of organic acid and having at least 50 wt % of ethanol is recovered from the column and passes at least in part to a catalytic dehydration zone for the production of ethylene. At least a portion of a column bottoms stream containing the neutralization product and having a pH in a range of from 5.5 to 6.5 returns from the distillation column to an aqueous fermentation broth in the fermentation zone.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE INVENTION

Figure 1:
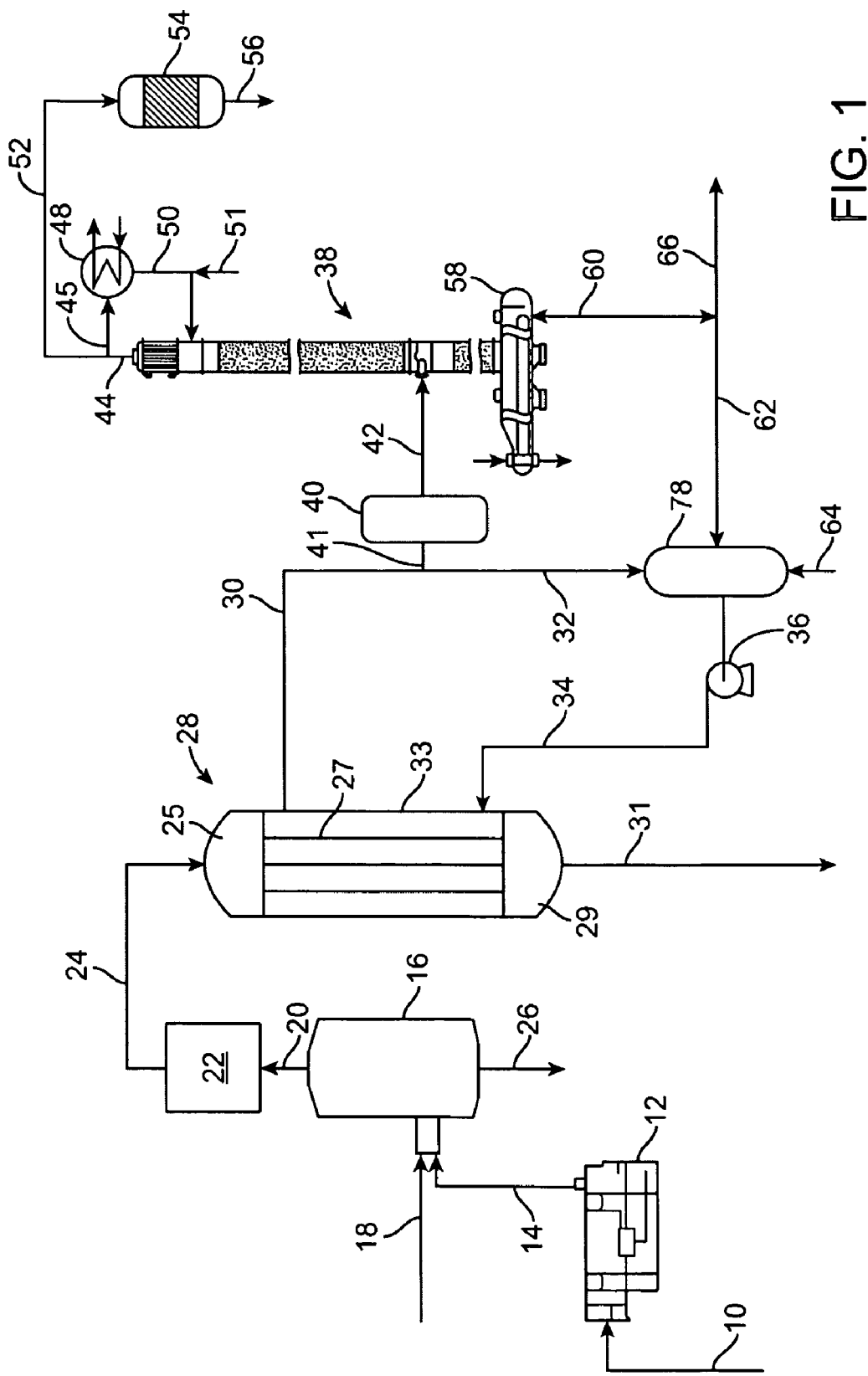
FIG. 1 is a schematic drawing of a process flow arrangement for producing ethanol from a biomass via gasification fermentation and separation in a separation zone.

This invention finds ready application to the production of alcohols, particularly ethanol with by-product acetic acid, and other products from a feed gas stream. This invention utilizes feed gas in the form of syngas. The term syngas as used herein means the primary components of CO, and/or $H_2$, and $CO_2$, individually or in combination with each other, or with other gaseous components. The other components often include $CH_4$, $N_2$, $NH_3$, $H_2S$, and other trace gases, or the like. A gasifier will ordinarily produce the syngas from biomass in the form of wood, switchgrass, corn stover and other waste materials. Any gas stream containing the primary components regardless of source will meet the definition of syngas for the purposes of this description.

Conversion of syngas using microorganisms is well known. For example, in a recent book concise description of biochemical pathways and energetics of such bioconversions have been summarized in "Electron Transport System in Acetogens," by A. Das and L. G. Ljungdahl, and "Diverse Physiologic Potential of Acetogens," by H. L. Drake and K. Kusel, appearing respectively as Chapters 14 and 13 of *Biochemistry and Physiology of Anaerobic Bacteria*, L. G. Ljungdahl, Ed., Springer (2003). Any suitable microorganisms that have the ability to convert the syngas components of CO, $H_2$, $CO_2$, individually or in combination with each other, or with other components that are typically present in syngas, may be utilized. Suitable microorganisms and/or growth conditions may include those disclosed in U.S. patent application Ser. No. 11/441,392, filed May 25, 2006, entitled "Indirect or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385, filed Aug. 31, 2006, entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms include the anaerobic bacteria *Butyribacterium methylotrophicum*, having the identifying characteristics of ATCC 33266 which can be adapted to CO and used. This enables the production of n-butanol as well as butyric acid as taught in the references: "Evidence for Production of n-Butanol from Carbon Monoxide by *Butyribacterium methylotrophicum*," in *Journal of Fermentation and Bioengineering*, vol. 72, 1991, pp. 58-60; and "Production Of Butanol And Ethanol from Synthesis Gas via Fermentation," in *FUEL*, vol. 70, May 1991, pp. 615-619. Other suitable microorganisms include *Clostridium ljungdahli*, with strains having the identifying characteristics of ATCC 49587 as disclosed in U.S. Pat. No. 5,173,429 entitled "Biological Production of Ethanol from Waste Gases with *Clostridium*

*ljungdahlii*," and ATCC 55988 and 55989 as disclosed in U.S. Pat. No. 6,136,577 entitled "Biological Production of Ethanol from Waste Gases with *Clostridium ljungdahlii*." This will enable the production of ethanol as well as acetic acid. All of the above references are incorporated by reference herein in their entirety.

The microorganisms found suitable thus far for bioconversion for this invention require anaerobic growth conditions. Therefore, the bioconversion system employs suitable control and sealing methods to limit the introduction of oxygen into the system. Since the microorganisms contact the liquid that circulates through the bioreactor system, a suitable redox potential is maintained and monitored to insure anaerobic conditions. Anaerobic conditions in the liquid volume are usually defined as having a redox potential of less than −200 mV and preferably a redox potential in the range of from −300 to −500 mV. To further minimize exposure of the microorganisms to oxygen, the feed gas will preferably have an oxygen concentration of less than 1000 ppm, more preferably less than 100 ppm, and even more preferably less than 10 ppm.

The syngas components undergo conversion in a fermentation zone by contact with the microorganisms. Many known devices and equipment can effect gas transfer for contacting microorganisms with syngas in a fermentation zone. Any suitable bioreactor apparatus configuration for initial conversion of the syngas to bio-chemicals can be used in the fermentation zone. These systems all keep the microorganisms supplied with liquid from a fermentation broth. Similar devices and equipment for gas-liquid contacting are also known from waste treatment applications. Many of these conventional bioreactors and systems use agitators with specialized blades or configurations. In some others such as gas lift or fluidized beds, liquids or gases are circulated via contacting devices. Particularly suitable bioreactors retain the microorganisms in the form of a biofilm on a substrate surrounded by a fermentation broth. Such substrates include free floating media as described in U.S. Ser. No. 11/833,864 (filed Aug. 3, 2007) the content of which is hereby incorporated by reference.

To get high yields and production rates the cell concentrations in the bioreactor need to be high and this requires some form of cell recycle or retention. Conventional ways to achieve high cell retention includes filtration of the fermentation broth through microporous or nonporous membranes, returning the cells and purging the excess.

Cell retention by formation of biofilms or biolayers are a very good and often inexpensive ways to increase the density of microorganisms in bioreactors. This requires a solid matrix with large surface area for the microorganisms to colonize and form a biofilm that contains the metabolizing microorganisms in a matrix of biopolymers that the microorganisms generate. Trickle bed and some fluidized bed bioreactors make use of biofilms to retain microorganisms on solid surfaces while providing dissolved gases in the liquid by flow past the solid matrix.

Membranes constitute a class of useful substrates for cell retaining microorganisms in biofilms or biolayers to obtain the benefits of increased microorganisms density in bioreactors. The membrane offers a solid matrix with large surface area for an activated surface comprising the microorganisms that colonize and form a biofilm or biolayer to contain the metabolizing microorganisms in a matrix of biopolymers that the cells generate. These systems use microporous membranes or non-porous membranes or membranes having similar properties that transfer (dissolve) gases into liquids while concurrently serving as the support upon which the fermenting microorganisms grow in a concentrated layer. The membrane will also provide a phase separation between the syngas on one side of the membrane and the fermentation broth on the other side of the membrane. The biofilm class of membrane bioreactors appears best suited to the microorganisms on the liquid phase side of the membrane while the biolayer class of bioreactors is typically differentiated by retaining the microorganisms principally in the gas phase side of the membrane.

U.S. patent application Ser. No. 11/781,717, filed Jul. 23, 2007; U.S. patent application Ser. No. 11/833,864, filed Aug. 3, 2007; and U.S. patent application Ser. No. 11/972,454, filed Jan. 10, 2008, (the contents of which are hereby incorporated by reference) disclose the biolayer type of membrane bioreactor. These references describe a membrane based bioreactor wherein anaerobic bacteria that have the ability to convert syngas to ethanol or other liquids have formed biofilms on the surface of hydrophobic membranes that is closest to the liquid phase such that the syngas fed crosses the membrane from the gas phase side to the biofilm on the surface of the membrane's liquid phase side. Such a bioreactor system has been able to directly convert the primary components of synthesis gas, CO, and $H2/CO_2$ to ethanol and other liquid products such as butanol, hexanol acetic acid, and butyric acid. In these systems the gas typically flows through a porous region of a hydrophobic membrane and then reaches the hydrophilic biofilm.

Numerous membrane composition and systems are available to serve as substrates for the biofilm. Hollow fiber membrane configurations are particularly useful. Suitable hydrophobic microporous hollow fiber membranes have been used for degassing applications to remove oxygen, carbon dioxide, and other gases from water and other liquids. An example of commercial membrane modules for such applications is the Liqui-Cel® membrane contactor from Membrana (Charlotte, N.C.), containing the polypropylene (PP) X40 or X50 hollow fibers. CELGARD® microporous PP hollow fiber membrane, containing the X30 fibers, is also available from Membrana for oxygenation applications. Liqui-Cel® membrane modules suitable for large scale industrial applications have large membrane surface areas (e.g., 220 $m^2$ active membrane surface area for Liqui-Cel Industrial 14×28). Some characteristics of these fibers are given in the Table 1 below.

TABLE 1

|  | X30 | X40 | X50 |
|---|---|---|---|
| Porosity (nominal) | 40% | 25% | 40% |
| Pore Size | 0.03 μm | 0.04 μm | 0.04 μm |
| Internal Diameter | 240 μm | 200 μm | 220 μm |
| Outer Diameter | 300 μm | 300 μm | 300 μm |
| Wall Thickness | 30 μm | 50 μm | 40 μm |

To prevent wetting of pores during operations, some composite membranes have been developed by the membrane suppliers. The SuperPhobic® membrane contactor from Membrana keeps the gas phase and liquid phase independent by placing a physical barrier in the form of a gas-permeable non-porous membrane layer on the membrane surface that contacts the process liquid. The SuperPhobic® 4×28 module contains 21.7 $m^2$ membrane surface area. Another composite hollow fiber membrane with an ultra-thin nonporous membrane sandwiched between two porous membranes is available from Mitsubishi Rayon (Model MHF3504) in the form of composite hollow fibers having a 34 $m^2$ membrane area per module.

Membranes made of poly(vinylidene fluoride) (PVDF), polyethylene (PE), PP, poly(vinyl chloride) (PVC), or other polymeric materials are also suitable. The typical pore size is in the range of 0.03 to 0.4 µm. The typical hollow fiber outer diameter is 0.5 to 2.8 mm and inner diameter 0.3 to 1.2 mm. Hollow fiber membranes made of polymethylpentene (PMP) can be used. These PMP hollow fibers are non-porous and of either the skinned asymmetric or dense type as described in "Evaluation of Plasma Resistant Hollow Fiber Membranes for Artificial Lungs" by Heide J. Eash et al. ASAIO Journal, 50(5): 491-497 (2004) and U.S. Pat. No. 7,118,672 B2.

Kubota Corporation (Tokyo, Japan) markets submerged membrane systems for membrane bioreactors. These membranes are of the flat-plate configuration and made of PVC with a pore size of 0.4 µm. Each membrane cartridge has 0.8 m$^2$ membrane surface area, and a Model EK-400 membrane unit, containing 400 membrane cartridges, has a total membrane area of 320 m$^2$.

As opposed to the biofilm type system, a biolayer type of bioreactor will retain microorganisms in or about a porous membrane layer that is closest to the gas phase side of the membrane such that the syngas the syngas has direct contact with microorganism and the liquid crosses the membrane from the membrane's liquid phase side. The biolayer constitutes a membrane structure that provides pores to promote and control the growth of microorganism colonies therein while also exposing a surface over which to directly feed the microorganisms with syngas. Simultaneously another layer of the membrane having less permeability than the biolayer, herein referred to as a hydration layer, permeates liquid from the opposite side of the membrane that contacts the gas phase. In a normal operating mode for a biolayer system liquid does not permeate past the biolayer or the membrane's liquid phase side. The liquid products produced in the biolayer on the membrane's gas contact side pass through the membrane and into a liquid stream that recovers the desired liquid products while also supplying nutrients to the biolayer in the reverse direction of liquid product flow.

In the biolayer operation the gas side pressure is normally slightly higher than the liquid pressure to prevent convective liquid flow from the hydration layer (liquid) side to the open surface (gas) of the gas contacting side. The higher pressure also avoids formation of a liquid layer at the cell/gas interface, which would impede gas transfer to the cells. U.S. Ser. No. 12/258,193 filed Oct. 24, 2008 (the contents of which are hereby incorporated by reference) disclose specific methods of operating biolayer membrane systems to improve product and nutrient interchange by regular laving of the liquid phase in the membrane and flushing the biolayer by periodic purging of liquid onto the membrane's gas phase surface.

The biolayer defines the biopores for retaining the microorganisms in direct contact with the syngas. The biopores require an effective diameter of at least 1 µm over at least a portion of its length. The term effective diameter refers to the open cross-sectional area of a regularly shaped pore that would provide the same cross-sectional area. The pores need not have a uniform cross-section and biopores having an effective diameter of 1 µm over at least a third of its length are suitable. The biopores in the biolayer of the membrane usually have an effective diameter substantially greater than 1 µm, preferably in the range of 2 to 100 µm, and most preferably in the range of 5 to 50 µm. Typical depths of the biopores range from 50 to 500 µm which generally corresponds to the thickness of the biolayer.

The hydration layer can have restricted liquid permeability with respect to the biolayer. The restricted permeability prevents excessive fermentation liquid from migrating into the biolayer during normal operation of the system and interfering with contact between the gas and microorganisms. In most cases, the hydration layer is a higher density material than the biolayer that restricts liquid flow while also occluding the internal end of the biopores to block migration of the microorganisms into the fermentation liquid.

The biolayer and hydration layer are described as single layers, but either or both can include several layers. Asymmetric membranes provide a highly useful support element for the biolayer type bioreactor. Asymmetic membranes are known for use in a variety of membrane separations processes such as ultra and nano filtration. Asymmetric membranes are typically hydrophilic and have a relatively tight semi permeable "skin" layer on one side supported on a porous polymer layer. U.S. Pat. Nos. 4,442,206 and 4,440,853 show the use of the polymer layer in an asymmetric membrane to immobilize microorganisms for certain biological processes that use soluble carbon sources. U.S. Ser. No. 12/036,007 filed Feb. 28, 2008 discloses the use of asymmetric membranes to produce alcohols from syngas in a bioreactor that retains microorganisms as a biolayer in or about the surface of a membrane.

Particularly suitable forms of asymmetric membranes are porous membranes with a tight (i.e., having small pores) thin "skin" on one surface of the membrane that provides the hydration layer and a relatively open support structure underneath the skin that provides the biolayer and defines the biopores. The skin will typically comprise a semi-permeable layer having a thickness of from 0.5 to 10 µm. The skinned asymmetric membrane can include an "integrally skinned" membrane prepared by using phase inversion of one polymer or a composite membrane, where a thin layer of a certain material is formed on top of a porous sublayer of a same or different material. General descriptions of asymmetric membranes and methods of their preparation can be found in the literature (e.g., M. Cheryn, *Ultrafiltration and Microfiltration Handbook*, Technomics Publishing Company, Lancaster, Pa., 1998; and M. Mulder, *Basic Principles of Membrane Technology*, 2$^{nd}$ Edition, Kluwer Academic Publishers, Norwell, Mass., 1996)

Hollow fiber membrane modules containing asymmetric ultrafiltration membranes are commercially available from a number of membrane manufacturers. For example, the Kros-Flo® Max Module Model KM5S-800-ON from Spectrum Laboratories (Rancho Dominguez, Calif.) has 22.0 m$^2$ membrane surface area of asymmetric polysufone hollow fiber membranes with 0.5 mm fiber inner diameter, a tight skin on the lumen side, and a pore rating of 50 kDa. ROMICON® polysulfone hollow fiber membranes available from Koch Membrane Systems (Wilmington, Mass.) are also asymmetric with the tight skin on the lumen side. ROMICON cartridge Model HF-97-43-PM50 is a 6-inch module containing fibers of 1.1 mm inner diameter and 50 kDa nominal MWC at 9.0 m$^2$ total membrane surface area.

Membranes of the various geometries and compositions described above may be used in arrangements of unitary arrays or assemblies of varied composition in the process of this invention. Any suitable technique can be used to collect and provide the necessary assembly of individual membrane elements. In such membranes the gas and liquid must be circulated into direct and intimate contact with opposing surface of the membrane. Liquid is passed in the liquid side of the membranes via pumping, stirring, or similar means to remove the alcohol, organic acid and other soluble products formed; the products are recovered via a variety of suitable methods.

Syngas may flow through the gas chamber or channels of the bioreactor system continuously or intermittently. The feed gas pressure is in the range of 1 to 1000 psig, preferably 5 to 400 psig, and most preferably 10 to 200 psig. The differential pressure between the liquid and gas phases is managed in a manner that the membrane integrity is not compromised (e.g., the burst strength of the membrane is not exceeded) and the desired gas-liquid interface phase is maintained.

Membranes when arranged in modules provide a large surface area for retention of a biofilm or biolayer particularly when the membranes are in the form of hollow fibers. A number of the membrane modules can be located in a closed membrane vessel so that a very large total membrane surface area can be achieved with a small number of membrane vessels, simplifying plant design and reducing costs. The membrane vessel can be round, square, rectangular or any other suitable shape with gas-tight cover plates on the top. Those skilled in the art will appreciate that the membrane modules can have any cross section as desired for a particular purpose, such as round, rectangular, square, or any other cross section that accommodates a desired pitch and/or spacing.

Typically the plurality of membrane modules are two-headed membrane modules having a first potted end spaced apart from a second potted end, the first potted end is operably connected to one end of the hollow fibers and the second potted end is operably connected to the other end of the hollow fibers to allow the process liquid to flow through the hollow fiber lumens from the first potted end to the second potted end.

All forms of the bioreactors for use in this invention will include a liquid phase comprising a fermentation broth that provides nutrients to the microorganisms and receives the liquid products from the fermentation that include alcohol and organic acid produced by the microorganisms. The process recovers a portion of the fermentation broth as a fermentation stream that enters the separation zone for concentration of liquid products contained therein. Bioreactors that use a continuous stirred tank or a gas lift operation maintain a relatively large inventory of fermentation broth from which to withdraw the fermentation stream containing alcohol and organic acid. Membrane type bioreactor systems normally circulate the fermentation broth in a recycle loop from which the fermentation stream may be withdrawn. The separation zone of this process in addition to increasing the concentration of alcohol in the fermentation broth also provides a convenient means of neutralizing the concentrated liquid products and returning neutralization product to the bioreactor. The separation zone employs at least one separation column to effect these results but may include multiple separation vessels in the form of stripper and/or distillation columns.

The separation section will receive a broth with a low alcohol concentration. The low alcohol tolerance of most microorganisms results in the broth from the bioreactor having a low alcohol concentration. Thus the alcohol concentration of the fermentation broth typically ranges from 1 to 6% and more typically in a range of from 2 to 4 wt %. The separation section will raise the alcohol concentration to a minimum of 50 wt % and more desirably to 70 to 80 wt %.

In the simplest form of the separation zone a column input stream comprising the fermentation stream, or a portion thereof that has undergone prior separation, will enter a separation column, preferably a distillation column that separates the input stream into upper and lower column fractions. A portion of an overhead stream comprising an upper column fraction circulates through a partial reflux condenser. A neutralization additive is injected into the condenser recycle loop to provide additive to eliminate most free acid in the upper stages of the column and the resulting vapor. The net column overhead now contains a low organic acid level and a concentration of water vapor less than 50 wt % that may be sent directly to a vapor phase alcohol dehydration zone for production of corresponding olefins or for further separation to reduce its water content before passing to the dehydration zone. The net column bottoms from the lower column fraction contains the resulting neutralization product that supplies neutralization product to the inventory of fermentation broth via its return thereto.

The separation zone can include multiple columns and as well as other separation devices so long as separation zone contains at least one column that receives the neutralization additive at a location that eliminates most free acid from its upper stages and provides a fraction that can return the neutralization product to the fermentation broth inventory. For example the fermentation stream may flow into a stripping column that produces a stripping column overhead having an alcohol concentration of about 50 wt %. The stripping column overhead serves as a partial reflux that also receives an injection of the neutralization additive before entering the upper end of the distillation column. The distillation column can produce overhead stream with an alcohol concentration in the range of 70 to 80 wt % that passes to an alcohol dehydration zone. The bottom fraction from the distillation column supplies the resulting neutralization product to fermentation broth inventory via the net bottoms from the distillation column.

The separation zone may operate the columns under a variety of conditions. Operating distillation column under vacuum eliminates high temperature requirements for bottoms stream that could result in the formation of toxic by-products. Thus, the majority of the column bottoms can return directly to the bioreactor. A small fraction of the column bottoms may undergo purging of acetates and other insolubles via an anaerobic digestor that converts these materials to methane. Advantages also derive from the limited number of phase changes from the low operating temperatures of a vacuum distillation column and the downstream processing of the ethanol overhead in the permeation units. Operation of a vacuum distillation column at moderate temperatures reduces the need for reflux over conventional columns and minimizes the vapor-liquid phase changes.

In another form the separation zone may incorporate a flash zone or stripping column that initially receives the fermentation stream. The typically low concentration of the alcohol stream to which this invention applies makes a flash step particularly useful. Since the alcohol concentration at typical equilibrium conditions is 9 to 12 times greater in the vapor phase than in the liquid phase of a flash step, a flash step can provide a highly efficient enrichment of the alcohol containing stream before it enters the separation column. The flash zone may receive all or only a portion of the fermentation broth that passes to the stripping column for recovery of the ethanol. Most bioreactor arrangements will employ a circulation loop to circulate fermentation broth around the bioreactor and the flash zone may provide part of the broth circulation. The simplicity of the flash zone may also permit its use as part of the purification step to provide dilute ethanol to the stripping column. To operate, the flash zone basically requires only a heat addition equal to the latent heat of vaporization.

A wide range of alkaline material can serve as additives for the single purpose of neutralization, but preferably the additive will serve a complimentary function in the fermentation zone. The preferred neutralization additive comprises sodium hydroxide. Other neutralization additives for injection into the distillation zone include potassium hydroxide, ammonium hydroxide, calcium hydroxide and mixtures thereof.

After neutralization of organic acids the alcohol containing stream passes from the separation zone to an alcohol dehydration zone for the production of olefins. This invention is not limited to any particular alcohol dehydration zone, but provides an alcohol containing stream particularly suited for vapor phase dehydrogenation of alcohols to olefins and in particular the dehydration of ethanol to ethylene. The acid free stream from the separation will typically have a water concentration of from 20 wt % to 60 wt % and preferably a water concentration of from 20 wt % to 40 wt %.

A wide variety of catalysts are known for the dehydration of alcohols to olefins. The preferred catalysts have been alumina or alumina-silica, such as alumina and magnesia deposited on a porous silica carrier. The catalyst composition may also comprise a crystalline aluminosilicate zeolite type of natural or synthetic origin, as described, for example, in U.S. Pat. No. 4,727,214, the entirety of which is incorporated herein by reference. Optionally, the catalyst composition comprises an activated alumina catalyst containing one or more of: an alkali metal, sulfur, iron and/or silicon, as described in U.S. Pat. No. 4,302,357, the entirety of which is incorporated herein by reference. Other catalysts include a ZSM-5 and/or a ZSM-11 catalyst composition as described in U.S. Pat. No. 4,698,452, the entirety of which is incorporated herein by reference. In another embodiment, the catalyst composition can comprises a substituted phosphoric acid catalyst, as described in U.S. Pat. No. 4,423,270, the entirety of which is incorporated herein by reference.

Many of these same catalyst find particular utility in the dehydration of ethanol to ethylene (ETE). The ETE catalyst composition is selected from the group consisting of: silica-alumina, alumina (including activated alumina), activated clays, solid phosphoric acid, and a metal sulfate. Ethylene production via catalytic dehydration of ethanol (ETE) over $TiO_2/\gamma-Al_2O_3$ catalysts in multi-microchannel reactors is also known. Optionally, the ETE catalyst composition comprises a metal oxide selected from the group consisting of: $SiO_2$, $ThO_2$, $Al_2O_3$, $W_2O_4$, and $Cr_2O_3$. Other potential ethanol to ethylene catalyst compositions that may be implemented in the present invention include, but are not limited to, alumina and magnesia deposited on a porous silica carrier (Haggin, C & EN, May 18, 1981, pp. 52-54), Bauxite activated with phosphoric acid (Chem. Abst., 91, 12305 (1979)), SynDol (N. K. Kochar, R. Merims, and A. S. Padia, Chem. Eng. Progr., June, 1981, 77, 66-70), and polyphosphoric acid, (Pearson et al., Ind. Eng. Chem. Prod. Res. Dev., 19, 245-250 (1980)).

In an alcohol dehydration process of this invention the alcohol containing feed can comprise greater than about 50 weight percent alcohol, more preferably greater than about 70 weight percent alcohol, and most preferably greater than 80 weight percent alcohol, based on the total weight of the alcohol-containing feedstock. Optionally, the alcohol containing feedstock may comprises one or more organic compounds containing at least one oxygen atom in addition to ethanol.

For example, in dehydrogenation of ethanol the alcohol containing feedstock optionally comprises, in addition to ethanol, one or more other alcohols, preferably aliphatic alcohols where the aliphatic moiety of the alcohol(s) has from 1 to 10 carbon atoms, preferably from 1 to 6 carbon atoms, and most preferably from 1 to 4 carbon atoms. The alcohols useful as feedstock in addition to the ethanol in the process of the invention include lower straight and branched chain aliphatic alcohols and their unsaturated counterparts. Non-limiting examples of possible oxygenates (in addition to ethanol) that may be included in the ETE feedstock include methanol, n-propanol, isopropanol, methyl ethyl ether, DME, diethyl ether, di-isopropyl ether, formaldehyde, dimethyl carbonate, dimethyl ketone, acetic acid, and mixtures thereof. The ETE feedstock also optionally comprises a minor amount of acetaldehyde.

The various feedstocks discussed above are converted primarily into one or more olefins. The olefins or olefin monomers produced from the feedstock typically have from 2 to 8 carbon atoms, preferably 2 to 6 carbon atoms, still more preferably 2 to 4 carbons atoms, and most preferably ethylene and/or propylene In a preferred embodiment, the feedstock, which ideally comprises ethanol, is converted in the presence of a silica-alumina catalyst composition into olefin(s) having 2 to 6 carbons atoms, preferably 2 to 4 carbon atoms, and most preferably ethylene.

Typically the alcohol containing stream from the separation section will contain adequate amounts of water for diluent purposes. Nevertheless, the alcohol containing feedstock, in one embodiment, contains one or more added diluents, typically used to reduce the concentration of the feedstock. The diluents are generally non-reactive to the feedstock or the catalyst composition and include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen.

The diluent may be used either in a liquid or a vapor form, or a combination thereof. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25.

The alcohol dehydration process for converting the alcohol feedstock, especially a feedstock containing ethanol, is carried out in a reaction process in a reactor, where the process is a fixed bed process or a fluidized bed process (includes a turbulent bed process), preferably a continuous fluidized bed process. The process also employ a tubular reactor or a multi-bed stage reactor. Optionally, the reaction process is a fast-fluidized reaction process. The process can take place in a specialized catalytic reactors such as hybrid reactors that have a dense bed or fixed bed reaction zones and/or fast fluidized bed reaction zones coupled together, circulating fluidized bed reactors, riser reactors, a reactive distillation column, and the like. Suitable conventional reactor types are described in for example Fluidization Engineering, D. Kunii and O. Levenspiel, Robert E. Krieger Publishing Company, New York, N.Y. 1977, which are all herein fully incorporated by reference.

In accordance with the preferred modes of this invention the alcohol containing feed is preheated and vaporized before entering the reactor. The feed is preferably heated to about 150 to 350 degrees C. The conversion temperature employed in the alcohol dehydration process preferably can be in a broad range of from 20 degrees C. to 450 degrees C. and preferably is in the range of from 360 degrees C. to 400 degrees C. An ETE conversion temperature preferably is in the range of from about 150 degrees C. to 400 degrees C.

The conversion pressure employed in the alcohol dehydration process varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 10 kPaa to about 500 kPaa.

The weight hourly space velocity (WHSV), particularly in a process for converting a feedstock containing ethanol in the presence of a silica-alumina catalyst composition within a reaction zone, is defined as the total weight of the ethanol excluding any diluents to the reaction zone per hour per weight of silica-alumina catalyst composition in the reaction zone. Typically, the WHSV ranges from about 0.1 to about 0.9 $hr^{-1}$.

DETAILED DESCRIPTION OF THE DRAWINGS

This invention is further described in the context of a bioconversion process for the production of ethanol and ethylene from CO and/or mixtures of $H_2/CO_2$. The description of the invention in a particular context does not restrict its application or claim coverage from other process applications that meet the criteria for its use.

FIG. 1 shows biomass source 10 passing into a dryer 12 and dried biomass 14 conveyed into a gasifier 16 where it contacts an oxygen source provided via a line 18. Gasification produces residual ash 26 that leaves the gasifier and a raw syngas stream carried by a line 20. The raw syngas undergoes a series of heat recovery and gas cleaning steps in zone 22 before line 24 carries it to a bioconversion zone in the form of a bioreactor 28.

Bioreactor 28 comprises a membrane type bioreactor. Line 24 delivers the feed gas containing CO, $H_2$, and $CO_2$ to a feed gas distribution chamber 25 that distributes the feed gas stream to the lumens of a plurality of tubular membranes elements 27. A collection chamber 29 collects an exhaust gas of unreacted feed gas components that leave the bioreactor 28 via a line 31. During the bioconversion, excess $CO_2$ is generated and this gas can diffuse back and dilute out the concentrations of CO and $H_2$ in the feed gas and thus reduce their mass transfer rates. Suitable systems may be used to reduce CO2 concentrations in the exhaust gas of line 31.

A tank 33 surrounds the outside of the tubular membrane elements 27 in the membrane supported bioreactor and retains a liquid for growth and maintenance of a biofilm layer on the outer surface of the membrane. The liquid in the tank is stirred to provide adequate mixing and sparged with a suitable gas, if necessary, to maintain a suitable gaseous environment.

A portion of the fermentation broth is withdrawn from tank 33 of bioreactor 28 via a line 30 to provide the ethanol effluent that is separated into the recycle broth and the dilute ethanol stream for recovery of the ethanol product. This ethanol effluent may be withdrawn from any convenient location of the bioreactor arrangement. The fermentation broth comprises an aqueous solution containing ethanol in a concentration of from 1 to 6 wt % and more narrowly in a range of from 2 to 4 wt % ethanol. The withdrawal rate of ethanol effluent depends on the particular bioreactor arrangement.

Most bioreactor arrangements include a broth circulation and recycle loop from which the broth that contacts the microorganism may be withdrawn to provide the ethanol effluent. FIG. 1 shows a recycle loop consisting of line 30 and lines 32 and 34. A pump 36 maintains circulation of the fermentation broth through the loop. Desired flow conditions within the bioreactor typically dictate the flow rate in the recirculation loop. For example in a membrane bioreactor the recirculation rate is selected to eliminate any significant liquid boundary layer that impedes mass transfer near the liquid-facing side of the membrane and while avoiding excessive shear that may severely limit the attachment of cells and formation of the biofilm on the membrane surface. For a biofilm arrangement the superficial linear velocity of the liquid, tangential to the membrane, should be in the range of 0.01 to 20 cm/s, preferably 0.05 to 5 cm/s, and most preferably 0.2 to 1.0 cm/s.

Line 41 draws off a portion of the fermentation broth from the line 30 of the recirculation loop and passes it to the distillation column 38 via lines 41 and 42 as a dilute ethanol stream. The volume of the dilute ethanol stream withdrawn from the recirculation loop is determined by the desired concentration of ethanol in the fermentation broth. Ethanol must be removed from the fermentation broth to preserve the metabolic processes of the microorganisms by keeping the ethanol below a concentration that inhibits their activity. Conversely, the overall efficiency of recovering ethanol from the broth improves with higher ethanol concentration. Depending on the microorganisms, an ethanol concentration of 2 to 4 wt % generally sets the best balance and typically at least 10 wt % of the circulating fermentation broth enters the distillation column as the dilute ethanol stream.

Before entering the distillation column the dilute ethanol stream may undergo purification in a purification zone 40 for the removal of biological materials and other dissolved matter. The purification zone may use any suitable means such as filtration or ultra-filtration to recover these materials. Microorganisms retained in the purification zone may be returned to the fermentor.

Ordinarily purification zone 40 supplies a liquid phase stream to distillation column 38. A step-down in pressure vaporizes at least a portion and preferably all of the liquid prior to entering column 38. A pressure regulator (not shown) will supply the step-down in pressure. In preferred form the liquid stream will pass through an expansion valve that vaporizes all of the liquid in line 42.

The distillation column separates the dilute ethanol stream into an overhead vapor stream 44 and an ethanol depleted bottoms stream that passes to the bottom of the column. The dilute ethanol stream of line 42 preferably enters the column near the lower stages of the column 38. When operating under vacuum conditions the distillation column will normally operate at a pressure of about 200 torr to 500 torr. Separation requirement of the column will vary with the ethanol concentration of the entering dilute ethanol stream. At higher ethanol concentration the vacuum column will normally provide at least 10 stages of separation. More typically the column will have about 15 stages of separation and will operate in the range of 300 to 400 torr. Ordinarily the column when in vacuum mode will provide an ethanol concentration of at least 40 wt % and more often at least 50 wt % in the overhead vapor stream. At low concentrations, the vacuum conditions and stages of the separation will permit the column to operate with a relatively low maximum temperature of about 80 C.

A line 45 draws off at least a portion of the overhead vapor stream from line 44 as reflux for column 38. The ethanol concentration of the bioreactor effluent in line 42 and the desired ethanol concentration in overhead stream 44 will determine of reflux taken by line 45. Line 45 delivers the vapor stream to cooler 48 for partial condensation as reflux to column 38. Line 51 injects neutralization additive into line 50 for return of reflux and the introduction of neutralization additive into the upper stages returns reflux to the column 38.

Net overhead vapor taken from column 38 via line 52 provides the feed to an ethylene dehydration zone 54. The ethanol containing stream 52 may undergo further treatment and conditioning to provide appropriate product composition and characteristics prior to entering the dehydration zone 54. For example stream 52 may undergo further water removal steps via further rectification or permeation to adjust its water content. Dehydration zone 54 will contact the ethanol containing stream at vapor phase dehydration conditions with a suitable dehydration catalyst, typically an alumina deposited on a porous silica carrier, to produce a raw ethylene product stream recovered from dehydration zone 54 via line 56.

Reflux from line 50 reenters column 38 in its upper stages and introduces sodium hydroxide as the neutralization additive for circulation through the column. As the additive circulates through the column it reacts with the acetic acid from the fermentation stream to produce a sodium acetate as a neutralization product. The ethanol deficient fraction that also contains the sodium acetate leaves lower section of column 38 through reboiler section 58 and line 60 that removes a net column bottom stream. Heat from the contents of line 60 may be recovered for use other parts of the separation section (not shown).

The majority of the net column bottoms in line 60, typically more than 90% returns to the broth recirculation loop via a line 62 and a mixing chamber 78. A nutrient feed is added via line 64, as needed, to compensate for the amount of water removed from the separation step and to replenish nutrients needed to maintain the activity of the microorganisms. Chamber 78 provides any mixing of the various streams and components before they return to tank 33 via line 18. The flow of recycled fermentation broth from line 34 to the tank 33 provides the means of temperature and pH controls for the liquid, which contains nutrients needed to sustain the activity of the microorganisms.

A minor portion of the net bottoms are removed as a purge stream via line 66. These bottoms may be sent to a methane digestor to convert the soluble, colloidal and other organic waste to methane for energy recovery and to reduce the waster treatment load from the process.

In certain cases the use of a stripping column to provide an initial enrichment of the ethanol feed to the distillation step may improve the efficiency of the separation. The stripping column provides the most benefit where the ethanol concentration in the fermentation stream is less than 2 wt %. With the addition of the stripping column and suitable heat integration the distillation and dewatering steps of the vapor permeation units may effectively treat ethanol effluents with ethanol concentrations as low as 1.2 wt %.

Figure 2:
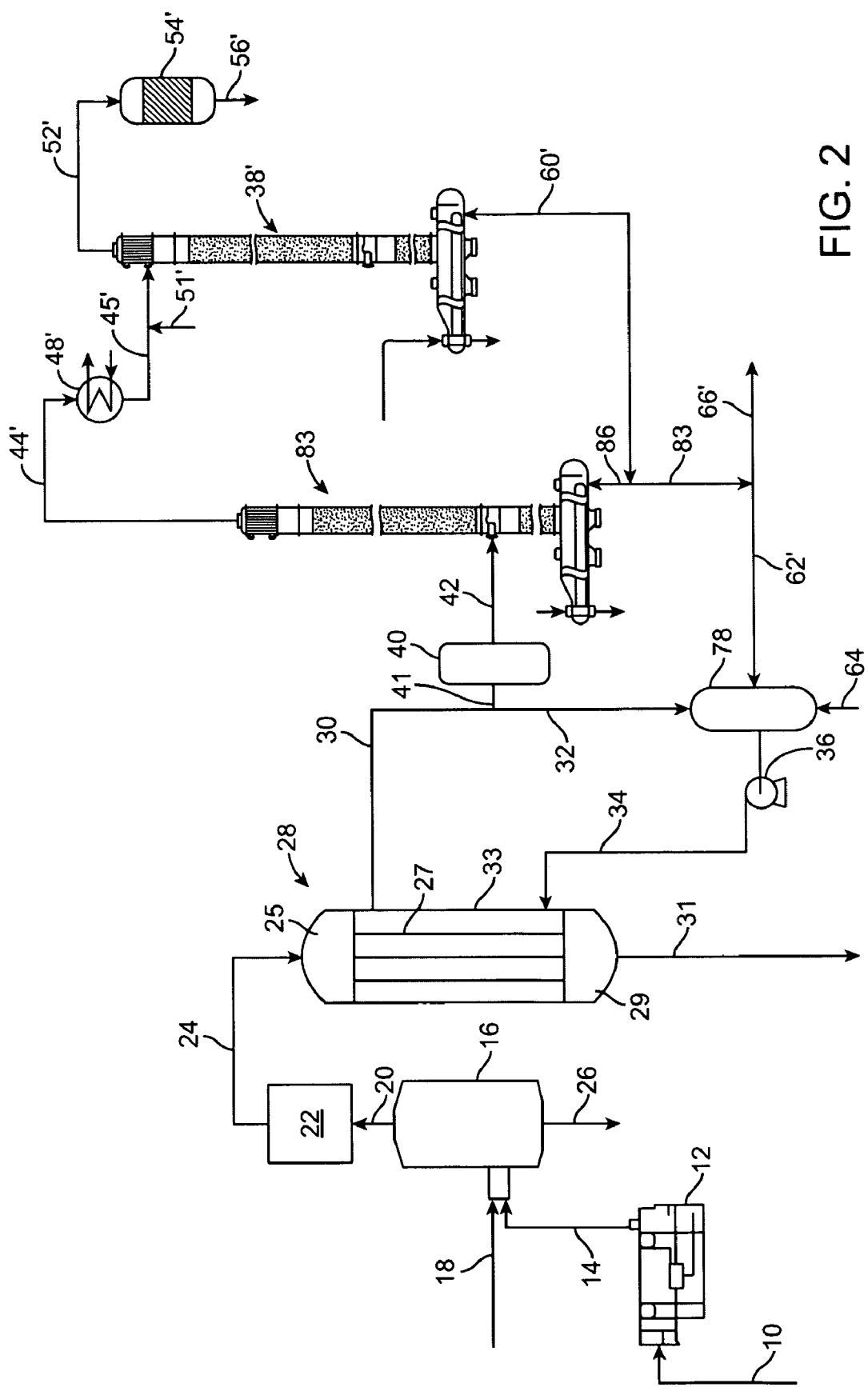
FIG. 2 is a modified arrangement of the drawing of FIG. 1 showing the addition of a stripping column to the separation zone.

FIG. 2 shows the arrangement of this invention with the addition of a stripping column. All similar elements of FIG. 2 have the same numbering as FIG. 1.

The separation zone as depicted in FIG. 2 includes a stripping column 83 that receives the fermentation stream of line 42. A line 86 carries the stripping column bottoms from a reboiler section 81 and combines the stripping column bottoms with the distillation column bottoms 60' into a line 83. As previously described a majority of the bottom stream contain the neutralization additive returns for circulation with the fermentation broth via line 62' while a small portion of the bottoms are separated as a purge taken via line 66'.

Line 44' carries overhead vapor from the stripping column 83 to cooler 48' for partial condensation to provide an input stream to distillation column 38'. Line 51' injects sodium hydroxide into line 45' as a neutralization additive and the partially condensed overhead from line 45' into the upper stages of column 38'.

The input from line 45' enters column 38' in its upper stages and introduces the neutralization additive for circulation through the column and production of sodium acetate as a neutralization product. The ethanol deficient fraction that also contains the sodium acetate leaves lower section of column 38' through line 60' that removes a net column bottom stream.

Net overhead vapor taken from column 38' via line 52' again provides the feed to an ethylene dehydration zone 54'. The inclusion of the stripping zone will usually raise the ethanol concentration of stream 52' such that it will need no further water removal before entering a dehydration zone 54.'

The invention claimed is:

1. Process for preparing an alcohol containing stream from an alcohol producing fermentation zone as a feed for an olefin reaction zone by removing organic acids, said process comprising:
    a) passing a fermentation stream produced in a fermentation zone to a separation zone, said fermentation stream comprising an alcohol, water and an organic acid;
    b) concentrating the alcohol and organic acid into an upper column fraction in said separation zone;
    c) injecting an additive for neutralization of said organic acid into contact with said upper column fraction;
    d) reacting said additive with said organic acid to produce a neutralized product that passes to a lower portion of a separation column within said separation zone;
    e) recovering a column overhead from said separation zone having an increased concentration of the alcohol and a reduced concentration of said organic acid;
    f) recovering a column bottoms stream containing said neutralization product; and,
    g) returning the column bottoms stream from said separation zone to an alcohol producing fermentation zone.

2. The process of claim 1 wherein the fermentation zone produces a fermentation stream comprising an ethanol containing stream and the column overhead stream passes to a reaction zone for the production of ethylene.

3. The process of claim 2 wherein the fermentation zone converts syngas components into ethanol, the fermentation stream includes acetic acid and the neutralization additive comprises sodium hydroxide.

4. The process of claim 3 wherein the neutralization product comprises sodium acetate and the bottoms stream mixes with an aqueous fermentation broth to supply sodium acetate to the fermentation zone.

5. The process of claim 4 wherein the fermentation zone produces a fermentation stream comprising water, 2 to 5 wt % ethanol, at least 0.3 wt % acetate and free acetic acid of at least 0.1 wt %; the column overhead stream comprises 70 to 80 wt % of ethanol and is relatively free of organic acid; and the reaction zone comprises a catalytic dehydration zone.

6. The process of claim 5 wherein the addition of sodium hydroxide neutralizes the column overhead to a pH of about 6.0.

7. The process of claim 1 wherein the fermentation zone contains microorganisms selected from the group consisting of *Clostridium ragsdalei, Butyribacterium methylotrophicum, Clostridium ljungdahlii, Clostridium carboxidivorans*, and combinations thereof and for the production of the liquid product selected from the group consisting of ethanol, n-butanol, hexanol, acetic acid, butyric acid, and combinations thereof.

8. The process of claim 1 wherein the separation column comprises a distillation column, at least a portion of the fermentation stream enters the distillation column and the columns bottoms stream is recovered from the distillation column.

9. The process of claim 8 wherein the fermentation stream enters a stripping column, the stripping column overhead passes to the distillation column and at least a portion of the distillation column bottoms stream and the stripping column bottoms stream are combined and returned to the fermentation zone.

10. The process of claim 1 wherein a portion of the separation column includes a reflux condenser and the additive is combined with the condensate reflux to the column to provide additive to the upper column fraction.

11. A process for reducing organic acid in an ethanol containing stream from a syngas fermentation zone, said process comprising:
   a) passing a syngas stream containing at least one of CO or a mixture of $CO_2$ and $H_2$ to a fermentation zone and converting at least a portion of the syngas to ethanol;
   b) withdrawing a fermentation stream comprising water, 2 to 5 wt % ethanol, at least 0.3 wt % acetate and free acetic acid of at least 0.1 wt %;
   c) passing the fermentation stream to a separation column and concentrating the ethanol and organic acids into an upper column fraction;
   d) injecting an additive for neutralization of said acetic acid into contact with said upper column fraction;
   e) reacting said additive with said acetic acid to produce a neutralization product that passes to a lower portion of the separation column;
   f) recovering a column overhead that is relatively free of organic acid and has at least 50 wt % of ethanol;
   g) recovering a column bottoms stream containing said neutralization product;
   h) returning at least a portion of the column bottoms stream to an aqueous fermentation broth in the fermentation zone.

12. The process of claim 11 wherein at least a portion of the column overhead stream passes to a catalytic dehydration zone for the production of ethylene.

13. The process of claim 12 wherein the neutralization product comprises sodium acetate and a sodium hydroxide is added in sufficient quantity as the additive to neutralize the column overhead to a pH of about 6.0.

14. The process of claim 13 wherein the fermentation zone contains microorganisms selected from the group consisting of *Clostridium ragsdalei, Butyribacterium methylotrophicum, Clostridium ljungdahlii, Clostridium carboxidivorans*.

15. The process of claim 11 wherein the separation column comprises a distillation column, at least a portion of the fermentation stream enters the distillation column, the columns bottoms stream is recovered from the distillation column, and a column overhead having an ethanol concentration of at least 70 wt % is withdrawn from the distillation column.

16. The process of claim 15 wherein the fermentation stream enters a stripping column, the stripping column overhead passes to the distillation column and at least a portion of the distillation column bottoms stream and the stripping column bottoms stream are combined and returned to the fermentation zone.

17. The process of claim 16 wherein the dehydration zone contacts the alcohol stream with a catalyst selected from the group comprising alumina or alumina-silica.

18. A process for producing ethylene by reducing organic acid in an ethanol containing stream from a syngas fermentation zone and dehydrating the ethanol in an ethanol dehydration zone, said process comprising:
   i) passing a syngas stream containing at least one of CO or a mixture of $CO_2$ and $H_2$ to a fermentation zone and converting at least a portion of the syngas to ethanol;
   j) withdrawing a fermentation stream comprising water, 2 to 5 wt % ethanol, at least 0.3 wt % acetate and free acetic acid of at least 0.1 wt %;
   k) passing at least a portion of the fermentation stream to a distillation column and concentrating the ethanol and organic acids into an upper column fraction;
   l) injecting an additive for neutralization of said acetic acid into contact with said upper column fraction;
   m) reacting said additive with said acetic acid to produce a neutralization product that passes to a lower portion of the distillation column;
   n) recovering a column overhead having at least 50 wt % of ethanol and is relatively free of organic acid;
   o) recovering a column bottoms stream containing said neutralization product and having a pH in a range of from 5.5 to 8.0 from the distillation column;
   p) returning at least a portion of the column bottoms stream to an aqueous fermentation broth in the fermentation zone; and,
   q) passing at least a portion of the column overhead stream to a catalytic dehydration zone for the production of ethylene.

19. The process of claim 18 wherein the additive comprises sodium hydroxide and the neutralization product comprises sodium acetate.

20. The process of claim 18 wherein the fermentation zone contains microorganisms selected from the group consisting of *Clostridium ragsdalei, Butyribacterium methylotrophicum, Clostridium ljungdahlii, Clostridium carboxidivorans*.

21. The process of claim 15 wherein the fermentation stream enters a stripping column, the stripping column overhead passes to the distillation column, at least a portion of the distillation column bottoms stream and the stripping column bottoms stream are combined and returned to the fermentation zone and a column overhead having an ethanol concentration at least 70 wt % is withdrawn from the distillation column.

* * * * *